(12) United States Patent
Mett et al.

(10) Patent No.: US 9,726,633 B2
(45) Date of Patent: Aug. 8, 2017

(54) ELECTROCHEMICAL GAS SENSOR SYSTEM

(71) Applicant: Dräger Safety AG & Co. KGaA, Lübeck (DE)

(72) Inventors: Frank Mett, Lübeck (DE); Kerstin Lichtenfeldt, Timmendorfer Strand (DE); Johanna Jörn, Lübeck (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 113 days.

(21) Appl. No.: 14/734,402

(22) Filed: Jun. 9, 2015

(65) Prior Publication Data

US 2015/0369773 A1   Dec. 24, 2015

(30) Foreign Application Priority Data

Jun. 21, 2014 (DE) .......................... 10 2014 009 365

(51) Int. Cl.
*G01N 27/404*  (2006.01)

(52) U.S. Cl.
CPC ................. *G01N 27/404* (2013.01)

(58) Field of Classification Search
CPC ............ G01N 27/404; G01N 27/4045; G01N 27/413; G01N 27/4168; G01N 27/407; G01N 27/4141; G01N 33/0009
See application file for complete search history.

(56) References Cited

U.S. PATENT DOCUMENTS

| | | | | |
|---|---|---|---|---|
| 5,855,750 A | * | 1/1999 | Kiesele .............. | G01N 27/4045 204/415 |
| 6,666,963 B1 | * | 12/2003 | Peng ................... | G01N 27/404 204/412 |
| 2004/0251144 A1 | * | 12/2004 | Chapples ........... | G01N 27/4045 205/775 |
| 2006/0230813 A1 | | 10/2006 | Tschuncky et al. | |

(Continued)

FOREIGN PATENT DOCUMENTS

| | | | |
|---|---|---|---|
| DE | 4132178 A1 * | 1/1993 | .......... G01N 27/404 |
| DE | 198 45 318 A1 | 4/2000 | |
| DE | 198 45 318 C2 | 9/2000 | |

(Continued)

*Primary Examiner* — Keith Hendricks
*Assistant Examiner* — Joshua Allen
(74) *Attorney, Agent, or Firm* — McGlew and Tuttle, P.C.

(57) ABSTRACT

An electrochemical gas sensor system (100) detects the concentration of a harmful gas in a measuring environment (70). The electrochemical gas sensor system (100) contains a voltage generator (19) and an electrochemical gas sensor (1). The electrochemical gas sensor (1) has a sensor housing (2) and a gas inlet (18). A measuring electrode (3), an auxiliary electrode (5), a reference electrode (17), a first generator electrode (13) and a second generator electrode (14) are in an electrolyte liquid (11) in the sensor housing (2). A salt (28) (halide) of a halogen is dissolved in the electrolyte liquid (11). The first generator electrode (13) and the second generator electrode (14) are connected to the voltage generator (19) to form a galvanic source. The galvanic source causes the salt (28) (halide) to react to form a halogen (28'). A defined, largely stable reference voltage potential becomes established on the reference electrode (17).

20 Claims, 2 Drawing Sheets

(56) References Cited

U.S. PATENT DOCUMENTS

2006/0237313 A1* 10/2006 Kiesele ................ G01N 27/404
 204/412
2011/0290671 A1* 12/2011 Mett .................. G01N 27/4045
 205/780.5

FOREIGN PATENT DOCUMENTS

| DE | 10 2005 017 445 A1 | 10/2006 |
| DE | 10 2009 010 773 A1 | 9/2010 |
| DE | 10 2010 021 975 A1 | 12/2011 |
| WO | 2010/063624 A1 | 6/2010 |

* cited by examiner

ELECTROCHEMICAL GAS SENSOR SYSTEM

CROSS REFERENCE TO RELATED APPLICATIONS

This application claims the benefit of priority under 35 U.S.C. §119 of German Patent Application DE 10 2014 009 365.4 filed Jun. 21, 2014, the entire contents of which are incorporated herein by reference.

FIELD OF THE INVENTION

The present invention pertains to an electrochemical gas sensor system.

BACKGROUND OF THE INVENTION

Electrochemical gas sensor systems are used for stationary or mobile monitoring tasks in industry, especially for monitoring harmful gas concentrations in chemical or petrochemical plants. In usual technical implementations, electrochemical gas sensor systems are composed of an electrochemical gas sensor with a sensor housing and a corresponding electronic operating and analyzing unit. Via a gas inlet, for example, a gas-permeable membrane, gas enters the sensor housing from a measuring environment. An electrochemical gas sensor with a measuring electrode, an auxiliary electrode, a reference electrode and a protective electrode for measuring oxygen is known from DE 198 45 318 C2. A measuring electrode, an auxiliary electrode, a reference electrode and a protective electrode are arranged in an electrolyte space filled with sulfuric acid as a liquid electrolyte. Both the measuring electrode and the protective electrode are also often called working electrode. The electrodes are electrically connected with an electronic operating unit, a so-called potentiostat. An equivalent electric potential is set on the measuring electrode and the protective electrode against a reference potential on the reference electrode by means of the potentiostat during the operation of the electrochemical gas sensor.

An electrochemical gas sensor with a measuring electrode made of carbon nanotubes and with an auxiliary electrode in an aqueous lithium bromide electrolyte for detecting hydrocyanic acid is known from DE 10 2010 021 975 A1. In an electrochemical gas sensor according to DE 10 2010 021 975 A1, the electric potential is set at the measuring electrode such that lithium bromide reacts to form bromine and dissolved bromine is thus present in the electrolyte. With this method for generating dissolved bromine, there is a basic current in the electrochemical gas sensor, which current depends on the electric potential set and has therefore an adverse effect on the sensitivity and the basic current stability of the electrochemical gas sensor.

SUMMARY OF THE INVENTION

An object of the present invention is to provide an electrochemical gas sensor system with improved stability of the basic current.

According to the invention, an electrochemical gas sensor system is provided for detecting the concentration of a harmful gas in a measuring environment. The electrochemical gas sensor system comprises a voltage generator and an electrochemical gas sensor. The electrochemical gas sensor has a sensor housing and a gas inlet. The gas inlet is designed to permit harmful gas to enter the electrochemical gas sensor from the measuring environment. An electrolyte liquid is contained in the sensor housing and an electrode configuration is arranged in the sensor housing. The electrode configuration comprises a measuring electrode, an auxiliary electrode, a reference electrode and a first generator electrode and a second generator electrode. The reference electrode is arranged between the first generator electrode and the second generator electrode. The first generator electrode and the second generator electrode are connected with the voltage generator. The voltage generator, the first generator electrode and the second generator electrode form a galvanic cell with the electrolyte liquid and with the voltage generator.

A device according to the present invention is formed by an electrochemical gas-measuring system. The electrochemical gas sensor system according to the present invention has an electrochemical gas sensor and a voltage generator. The device according to the present invention is designed to detect the concentration of a harmful gas in a measuring environment. The electrolyte liquid is electrically conductive and may also be, for example, an organic electrolyte, an ionic liquid or a combination of aqueous electrolyte liquid, ionic liquid and/or organic electrolyte.

The reference electrode, the measuring electrode and the auxiliary electrode are connected with an electronic operating and analyzing unit, the so-called potentiostat, during the operation of the gas sensor and of the gas sensor system. An equivalent electric potential is set or regulated by means of this potentiostat on the measuring electrode and the auxiliary electrode against a reference potential on the reference electrode. The voltage generator delivers a voltage, and an electrical field is formed between the first generator electrode and the second generator electrode. Due to the electric field, a defined reference potential becomes established on the reference electrode arranged between the first generator electrode and the second generator electrode. The electric field is largely independent from the electric potential on the measuring electrode and auxiliary electrode, which potential is set or regulated by the potentiostat. The basic current and the stability of the basic current of the electrochemical gas sensor system are thus advantageously affected only very slightly by the generator of the reference potential due to the present invention. The dependence of the setting of the reference potential is rather largely uncoupled from the setting of the electric potential on the measuring electrode. The basic current stability, improved by the present invention, has an advantageous effect on the sensitivity and/or the measuring accuracy of the electrochemical gas sensor system during the measurement of the harmful gas concentration. The defined reference potential on the reference electrode is determined essentially by the voltage of the voltage generator, the composition of the electrolyte liquid, as well as by the respective relative position in space of the reference electrode relative to the two generator electrodes. The current flow in the electrolyte liquid between the two generator electrodes depends on the available number of free charge carriers in the electrolyte liquid, the distance of the first generator electrode from the second generator electrode, the surfaces of the two generator electrodes and the properties of the voltage generator, such as the idle voltage and the internal resistance.

In a preferred embodiment, a halide is dissolved in the electrolyte liquid. Halides are various different compounds of a halogen, for example, iodine, chlorine, bromine, fluorine with metals, metalloids or nonmetals, in the form of iodides, chlorides, fluorides or bromides. Metal halides, for example, sodium chloride, potassium bromide, lithium bromide, silver bromide, silver fluoride, are also known as salts.

A bromide is dissolved in the electrolyte liquid in an especially preferred embodiment. The bromide is dissolved as lithium bromide in the electrolyte liquid in an especially preferred embodiment.

The voltage generator is preferably designed as a battery.

In a preferred variant, the voltage generator is designed such that the voltage or current can be set.

The voltage generator is designed as a settable voltage source in another preferred variant.

The voltage or current of the voltage generator is stabilized and/or regulated in another preferred variant.

In another preferred embodiment, the halide contained in the electrolyte liquid reacts by means of the galvanic cell to form a halogen, while a defined, largely stable reference potential becomes established on the reference electrode. The largely stable reference potential can be detected by measurement by means of an additional voltage measurement on the gas sensor, in which an additional reference electrode is inserted into the sensor housing and into the electrolyte liquid from the outside. The readiness of the generator electrodes to operate can thus also be checked indirectly in combination with the state of the voltage generator (battery capacity, battery voltage).

A reference electrode suitable for this purpose shall always be adapted to the electrochemical system used. A silver/silver bromide reference electrode (Ag/AgBr) is suitable for use as a reference electrode for an electrochemical system with an electrolyte in which a bromide, for example, lithium bromide, is dissolved.

In another preferred embodiment, a bromide contained in the electrolyte liquid reacts by means of the galvanic cell to form bromine, while a defined, largely stable reference potential becomes established on the reference electrode. This largely stable reference potential is found to be more positive by (935 mV±25 mV) relative to the reference electrode (Ag/AgBr). To operate the gas sensor, the potentiostat is set in this other preferred embodiment such that a potential difference in the range of 0 mV to −100 mV, preferably −40 mV to −60 mV, becomes established on the measuring electrode relative to the reference electrode.

In a preferred embodiment of the voltage generator, a set voltage is applied to a terminal of one of the two generator electrodes via a middle tap, the so-called slide, by means of a setting element, preferably a resistor potentiometer, in a parallel circuit with the voltage source, which potentiometer is connected to the plus pole and the minus pole of the voltage source, while the other terminal of the other of the two generator electrodes is connected with the plus pole or the minus pole of the voltage source.

In a preferred variant, the setting element, preferably designed as a settable resistor with a preferably low ohmic resistance, is arranged in a series connection with one pole of the voltage source towards the terminals of the two generator electrodes in order to form a settable voltage source.

In another preferred variant, a settable resistor with a preferably high ohmic resistance, is arranged as a setting element in a parallel connection with one pole of the voltage source towards the terminals of the two generator electrodes in order to form a settable voltage source.

The voltage generator is designed as a settable power source in another preferred variant.

Further possibilities or combinations of possibilities of setting the voltage or current are also covered in the sense of the present invention. This covers circuitry embodiments of voltage sources, voltage dividers, power sources by means of resistive and/or electronic resistors, as well as circuitry embodiments with relays or semiconductor components, for example, transistors, field-effect transistors, bipolar transistors, diodes, operational amplifiers, and ASICs.

In another preferred variant, the voltage generator, the voltage source or the settable power source is designed as part of the electronic operating and analyzing unit, is connected or coupled with the electronic operating and analyzing unit or is integrated in the electronic operating and analyzing unit.

Permeable nonwovens or nonwoven elements are arranged at the first and/or the second generator electrode in an especially preferred embodiment. These nonwovens or nonwoven elements are permeable to the electrolyte liquid and guide and/or transport the electrolyte liquid in the sensor housing to the electrodes.

In another preferred embodiment, the nonwovens permeable to the electrolyte liquid or the nonwoven elements permeable to the electrolyte liquid are arranged at the first and/or second generator electrode such that an installed position with predetermined distances of the generator electrodes from the reference electrode and with predetermined distances between the generator electrodes is obtained.

In another preferred embodiment, the first generator electrode and the second generator electrode as well as the reference electrode and the nonwovens permeable to the electrolyte liquid are enclosed by an inner housing impermeable to the electrolyte liquid.

The inner housing impermeable to the electrolyte liquid makes it possible to connect the generator electrodes and the reference electrode electrochemically directly to the measuring electrode and to connect the generator electrodes and the reference electrode electrochemically less directly to the auxiliary electrode.

In another preferred embodiment, at least one of the nonwovens permeable to the electrolyte liquid or the nonwoven element permeable to the electrolyte liquid is designed to transport the electrolyte liquid from the sensor housing to the area located between the first and second generator electrodes into the inner housing to the first and second generator electrodes.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
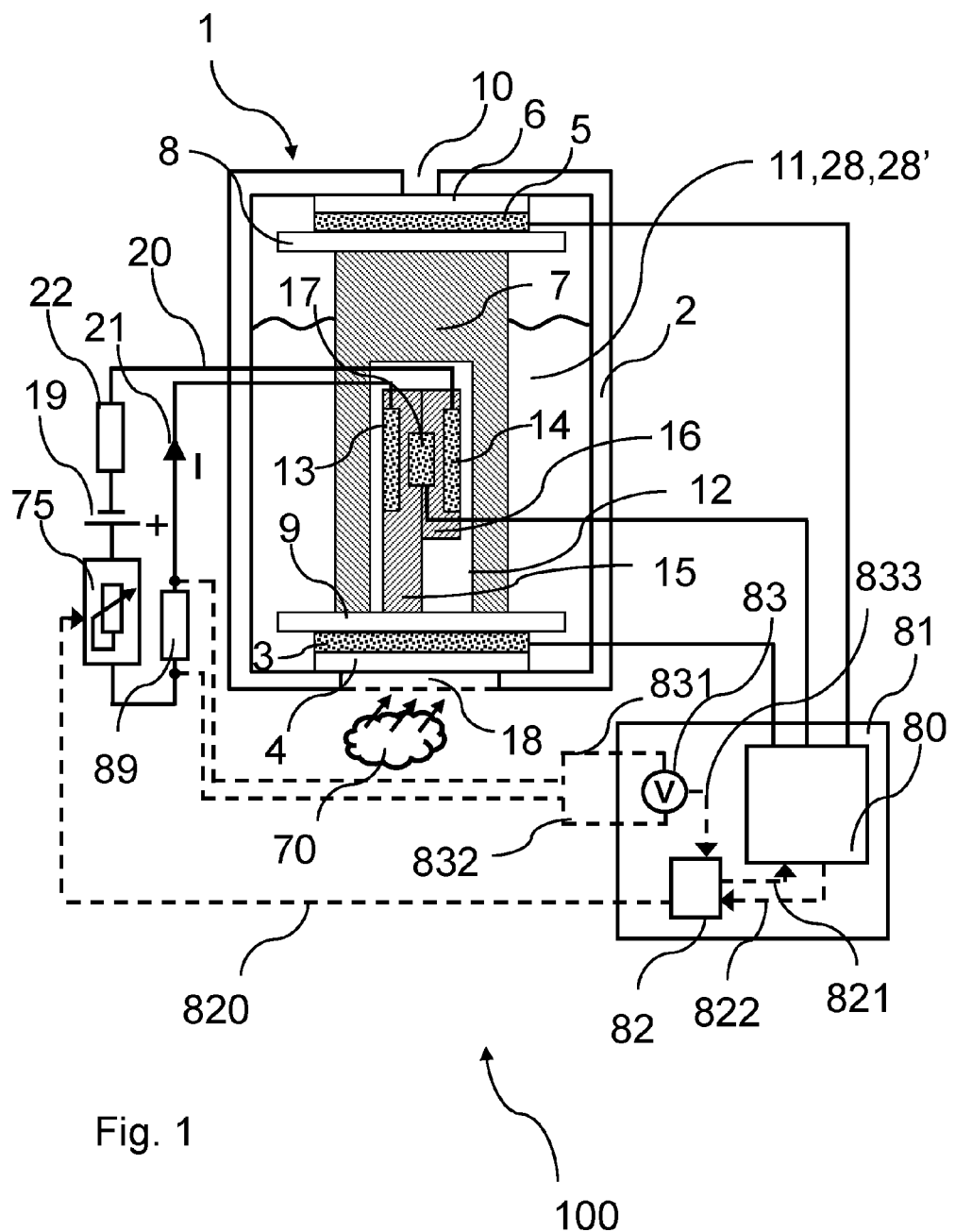
FIG. 1 is a schematic view showing a first gas sensor system with an electrochemical gas sensor with two generator electrodes in a first variant of a cylindrical design.

Referring to the drawings, FIG. 1 schematically shows in a side view a first electrochemical gas-measuring system 100 in a first variant 1 of an electrochemical gas sensor with a cylindrical sensor housing 2 and with a voltage generator 19. In the cylindrical sensor housing 2, a measuring electrode 3 is arranged on a first diffusion membrane 4 and an auxiliary electrode 5 on a second diffusion membrane 6. The sensor housing 2 is filled with an aqueous electrolyte liquid 11. Gas to be measured enters the cylindrical sensor housing 2 from a measuring environment 70 by means of a gas inlet 18 designed in the form of an opening in the cylindrical sensor housing 2 through the first diffusion membrane 4. The measuring electrode 3 and the auxiliary electrode 5 are kept at a fixed distance from one another by the arrangement of two nonwovens 8, 9 and by means of a wick 7. The pressure in the electrochemical gas sensor 1 is equalized with the environment 70 and the cylindrical sensor housing 2 is ventilated by means of a pressure-equalizing and ventilating opening 10 and through the second diffusion membrane 6. The measuring electrode 3 and the auxiliary electrode 5 are electrolytically connected with one another through the aqueous electrolyte liquid 11. An anode 13 as a first generator electrode and a cathode 14 acting as a second generator electrode are arranged laterally from two further nonwovens 15, 16 in the wick 7 in an inner housing 12 sealed for liquids. A reference electrode 17 is located between the nonwovens 15, 16. The nonwovens 15, 16 maintain the generator electrodes 13, 14 and the reference electrode 17 at a fixed distance from one another. The anode 13, the cathode 14 and the reference electrode 17 are arranged concentrically. The nonwovens 8, 9, 15, 16 and the wick 7 are designed such that they are permeable to the aqueous electrolyte liquid 11. The aqueous electrolyte liquid 11 is transported through the nonwoven 9 as well as at least one of the nonwovens 15, 16 into the inner housing 12 to the generator electrodes 13, 14 and to the reference electrode 17. A bromide 28 is dissolved in the aqueous electrolyte liquid 11. The anode 13 and the cathode 14 are connected to the voltage generator 19 designed as an electric voltage source. The measuring electrode 3, the auxiliary electrode 5 and the reference electrode 17 are connected electrically to a potentiostat 80, not shown in detail in this FIG. 1, or to an electronic operating unit 81 with integrated potentiostat 80, which electronic unit is not shown in detail in this FIG. 1. The anode 13 and the cathode 14 are connected with the electric voltage source 19 and the electrolyte liquid 11 to form a galvanic source. The galvanic source forms during the operation an electric circuit 20, in which an electric current 21 becomes established. An optional resistor 22 is preferably arranged connected in series with the generator electrodes 13, 14. The flow of the electric current 21 in the electric circuit 20 causes the bromide 28 contained in the aqueous electrolyte liquid 11 to react to form bromine 28'. The intensity of the electric current 21 is determined essentially by the preferred resistor 22 as well as by the resistance of feed lines and the internal resistance $R_i$ of the voltage source 19, which is not shown in this FIG. 1. The bromine 28' dissolved in the aqueous electrolyte liquid causes a largely stable electric potential to become established on the reference electrode.

In a special embodiment of the electrochemical gas-measuring system 100, the electric voltage source 19 is equipped with an optional setting element 75. This optional setting element 75 is designed to set or change the voltage of the voltage source 19. An optional control unit 82 is present in another optional variant of the electrochemical gas-measuring system 100. The optional control unit 82 is connected in this further optional variant of the electrochemical gas-measuring system 100 with the setting element 75 via a control line 820, which is drawn by a broken line in this FIG. 1. It is thus possible via the control line 820 to control the setting element 75 and, moreover, to set or change the voltage of the voltage source 19. The optional control unit 82 may be designed as a separate module or as a component of the electronic operating unit 81. A first data and control line 821, which is drawn by a broken line in this FIG. 1, and a second data and control line 822, which is drawn by a broken line in this FIG. 1, are preferably provided for a bidirectional data exchange between the control unit 82 and the potentiostat 80. This makes it possible to involve the potentiostat 80 in the setting or changing of the voltage of the voltage source 19 or even in the setting or changing of the voltage of the voltage source 19 by means of the electronic operating unit 81. This setting may be preferably used for presetting or configuration during the putting into operation of the electrochemical gas-measuring system 100 or preferably for fine adjustment during the operation of the electrochemical gas-measuring system 100. As a further optional expansion of the electrochemical gas-measuring system 100, an optional current-measuring resistor (shunt) 89 is arranged in the electric circuit 20. A voltage difference dropping over this optional current-measuring resistor 89 is sent by means of a first measuring line 831 and a second measuring line 832 to an optional measuring unit 83. The optional measuring unit 83 is designed, for example, in the form of a voltmeter, to measure the voltage difference dropping over the current-measuring resistor 89 and to determine the electric current 21 flowing in the circuit from this. The optional measuring unit 83 may be designed as a separate module or as a component of the electronic operating unit 81. In an especially preferred variant of this further optional expansion of the electrochemical gas-measuring system 100, the measuring unit 83 is connected via a third data or control line 833, drawn by broken line in this FIG. 1, with the control unit 82. There is an interaction of the potentiostat 80, measuring unit 83, control unit 82 and setting element 75, preferably arranged in the electronic operating unit 81, for setting or changing the voltage of the voltage source 19 in this especially preferred variant of this further optional expansion of the electrochemical gas-measuring system 100. It is thus possible to detect the electric current 21 actually flowing in the electric circuit 20, to directly or indirectly change the voltage of the voltage source 19 based on this and thus to set, control or regulate the electric current 21. An especially accurate setting of the electric potential on the reference electrode 17 is thus made possible with this especially preferred variant of this further optional expansion of the electrochemical gas-measuring system 100, because the potentiostat 80 can also be included in the setting or it can bring about itself the setting of the electric potential on the reference electrode 17.

Figure 2:
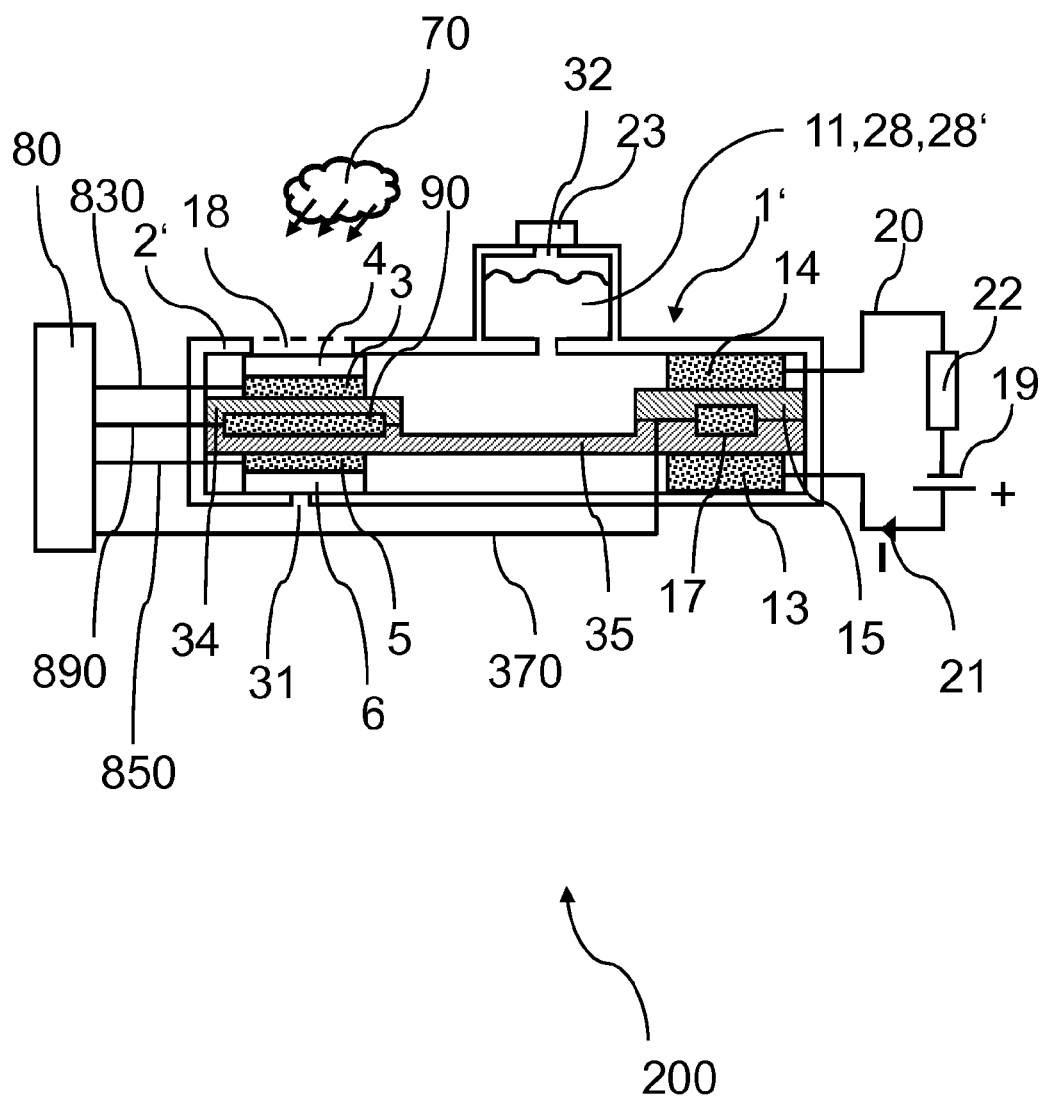
FIG. 2 is a schematic view showing a second gas sensor system with an electrochemical gas sensor with two generator electrodes in a second variant of a planar design.

FIG. 2 schematically shows in a side view a second electrochemical gas-measuring system 200 in an embodiment with an electrochemical gas sensor 1' with a planar sensor housing 2' and with a voltage generator 19. Identical components in FIG. 2 and FIG. 1 are designated in FIG. 2 by the same reference numbers as in FIG. 1.

The planar sensor housing 2' is filled with an aqueous electrolyte liquid 11. A measuring electrode 3 is arranged in the planar sensor housing 2' on a first diffusion membrane 4 and an auxiliary electrode 5 is arranged on a second diffusion membrane 6. The planar sensor housing 2' is vented through a ventilation opening 31 and through the second diffusion membrane 6. In addition, there is a protective electrode 90, which is arranged between the auxiliary electrode 5 and the measuring electrode 3. The protective electrode 90 is used to protect the measuring electrode 3 from substances diffusing from the aqueous electrolyte liquid 11 or from the ventilation opening 31 to the measuring electrode 3. Gas to be measured enters the planar sensor housing 2' from a measuring environment by means of a gas inlet 18 designed in the form of an opening in the planar sensor housing 2' through the first diffusion membrane 4. The measuring electrode 3, the protective electrode 90 and the auxiliary electrode 5 are maintained at a fixed distance from one another by means of two nonwovens 34, 35. The measuring electrode 3, the protective electrode 90, the auxiliary electrode 5 and the nonwovens 34, 35 are held as a stack in the planar sensor housing 2' between the first diffusion membrane 4 and the second diffusion membrane 6. The measuring electrode 3, the protective electrode 90 and the auxiliary electrode are connected with one another electrolytically by the aqueous electrolyte liquid 11. The pressure in the electrochemical gas sensor 1 is equalized with the atmospheric pressure of the environment 70 via a pressure equalization opening 32 and a third diffusion membrane 23. An anode is arranged in the planar sensor housing 2; as a first generator electrode and a cathode 14 is arranged as a second generator electrode. In addition to the nonwovens 34, 35, an additional nonwoven 15 is arranged in the planar sensor housing 2'. A reference electrode 17 is located between the nonwovens 15, 35. The nonwovens 15, 35 hold the two generator electrodes 13, 14 and the reference electrode 17 at a fixed distance from one another in the planar sensor housing 2'. The anode 13, the cathode 14 and the reference electrode 17 are planar and are preferably arranged in parallel to one another. The nonwovens 15, 34, 35 are designed as nonwovens permeable to the aqueous electrolyte liquid 11 and are used to wet the electrodes 3, 5, 17, 90, 13, 14 with the aqueous electrolyte 11. The nonwoven 35, in particular, is used to transport the aqueous electrolyte liquid 11 in the planar sensor housing 2' from the arrangement comprising the measuring electrode 3, the protective electrode 90 and the auxiliary electrode 5 to the arrangement comprising the generator electrodes 13, 14 and the reference electrode 17. The generator electrodes 13, 14, the measuring electrode 3, the protective electrode 90 and the auxiliary electrode 5, as well as the reference electrode 17 in the planar sensor housing 2' are thus connected with one another directly electrolytically by the aqueous electrolyte liquid 11. A bromide 28 is dissolved in the aqueous electrolyte liquid 11. The anode 13 and the cathode 14 are connected to the voltage generator 19 designed as an electric voltage source. The measuring electrode 3, the auxiliary electrode 5, the protective electrode 90 and the reference electrode 17 are connected electrically to a potentiostat 80, which is not shown in detail in this FIG. 2. The anode 13 and the cathode 14 are connected with the electric voltage source 19 and the electrolyte liquid 11 to form a galvanic cell. The galvanic cell forms an electric circuit 20 during the operation, in which an electric current 21 becomes established. An optional electric resistor 22 is preferably arranged connected in series with the generator electrodes 13, 14. The current flow 21 in the electric circuit 20 causes the bromide 28 contained in the aqueous electrolyte liquid 11 to react to form bromine 28'. The intensity of the current flow 21 is determined essentially by the preferred electric resistor 22 as well as by the resistance of the feed lines and the internal resistance $R_i$ of the voltage source 19, which is not shown in this FIG. 2. The bromine 28' dissolved in the aqueous electrolyte liquid causes a largely stable electric potential to become established on the reference electrode 17.

The special embodiments of the first electrochemical gas-measuring system 100 in FIG. 1 with variants and options for the arrangement and the interaction of setting elements 75 (FIG. 1), the electronic operating unit 81 (FIG. 1), the control unit 82 (FIG. 1), the current-measuring resistor 89 (FIG. 1), and the measuring unit 83 (FIG. 1) can also be extrapolated in a similar embodiment to the design of the second electrochemical gas-measuring system 200 and are thus also covered by the description of FIG. 1 in the sense of the present invention.

While specific embodiments of the invention have been shown and described in detail to illustrate the application of the principles of the invention, it will be understood that the invention may be embodied otherwise without departing from such principles.

APPENDIX

List of Reference Numbers

1 Electrochemical gas sensor in a first variant
1' Electrochemical gas sensor in a second variant
2 Cylindrical sensor housing
2' Planar sensor housing
3 Measuring electrode, working electrode
4 First diffusion membrane
5 Auxiliary electrode
6 Second diffusion membrane
7 Wick
8, 9 Nonwovens
10 Pressure equalization and ventilation opening
11 Aqueous electrolyte liquid
12 Inner housing
13 First generator electrode, anode
14 Second generator electrode, cathode
15, 16 Nonwovens
17 Reference electrode, reference electrode
18 Gas inlet, opening in the sensor housing
19 Voltage generator, electric voltage source
20 Electric circuit
21 Electric current I
22 Electric resistor
23 Third diffusion membrane
28 Bromide
28' Bromine
31 Ventilation opening
32 Pressure equalization opening
34, 35 Nonwovens
70 Measuring environment
75 Setting element (optional)
80 Potentiostat
81 Electronic operating unit
82 Control unit (optional)
83 Measuring unit (optional)
89 Current-measuring resistor/shunt (optional)
90 Protective electrode
100 First electrochemical gas-measuring system
200 Second electrochemical gas-measuring system
820 Control line (optional)
821 First data or control line (optional)
822 Second data or control line (optional)
831 First measuring line (optional)
832 Second measuring line (optional)
833 Third data or control line (optional)

What is claimed is:
1. An electrochemical gas sensor system for detecting the concentration of a gas in a measuring environment, the electrochemical gas sensor system comprising:
a voltage generator;

an electrochemical gas sensor comprising:
- a sensor housing with a gas inlet permitting a gas to enter the electrochemical gas sensor from the measuring environment;
- an electrolyte liquid in the sensor housing;
- an electrode configuration arranged in the sensor housing, the electrode configuration comprising a measuring electrode, an auxiliary electrode, a reference electrode and a first generator electrode and a second generator electrode, wherein:
  - the reference electrode is arranged between the first generator electrode and the second generator electrode;
  - the first generator electrode is electrically connected to a first terminal of the voltage generator and the second generator electrode is electrically connected to a second terminal of the voltage generator; and
  - the voltage generator, the first generator electrode and the second generator electrode form a galvanic cell with the electrolyte liquid.

2. An electrochemical gas sensor system in accordance with claim 1, wherein at least a halide compound or a halide is contained in the electrolyte liquid.

3. An electrochemical gas sensor system in accordance with claim 2, wherein:
- the halide compound contained in the electrolyte liquid or the halide contained in the electrolyte liquid is reacted by means of the galvanic cell to form a halogen; and
- a defined reference potential becomes established on the reference electrode.

4. An electrochemical gas sensor system in accordance with claim 2, wherein:
- the halide compound contained in the electrolyte liquid or the halide contained in the electrolyte liquid is bromide, and reacts to form bromine by means of the galvanic cell; and
- a defined, reference potential in the range of 935 mV±25 mV becomes established on the reference electrode.

5. An electrochemical gas sensor system in accordance with claim 1, wherein the voltage generator comprises at least one of a settable voltage generator, a settable voltage source and a settable power source.

6. An electrochemical gas sensor system in accordance with claim 1, wherein the voltage generator comprises a battery.

7. An electrochemical gas sensor system in accordance with claim 1, wherein a nonwoven, permeable to the electrolyte liquid, is arranged at the first generator electrode and a nonwoven, permeable to the electrolyte liquid, is arranged at the second generator electrode.

8. An electrochemical gas sensor system in accordance with claim 7, wherein the nonwovens, permeable to the electrolyte liquid and arranged each at the first generator electrode and at the second generator electrode, set an installed position with predetermined distances of the generator electrodes from the reference electrode and a predetermined distance between the generator electrodes.

9. An electrochemical gas sensor system in accordance with claim 8, wherein the first and second generator electrodes and the reference electrode and the nonwovens permeable to the electrolyte liquid are enclosed by an inner housing that is not permeable to the electrolyte liquid.

10. An electrochemical gas sensor system in accordance with claim 9, wherein at least one of the nonwovens, permeable to the electrolyte liquid, transports the electrolyte liquid from the sensor housing to an area between the first and second generator electrodes into the inner housing impermeable to the electrolyte liquid towards the first and second generator electrodes.

11. An electrochemical gas sensor system comprising:
- a sensor housing with a gas inlet;
- an electrolyte liquid in the sensor housing;
- a measuring electrode;
- an auxiliary electrode;
- a reference electrode;
- a voltage generator;
- an analyzing unit comprising a potentiostat connected to the measuring electrode, connected to the auxiliary electrode and connected to the reference electrode to set or regulate a potential on the measuring electrode and the auxiliary electrode with respect to a reference potential on the reference electrode; and
- an electric circuit, in which an electric current becomes established, the electric circuit comprising a first generator electrode electrically connected to a first terminal of the voltage generator, a second generator electrode electrically connected to a second terminal of the voltage generator, and applying a voltage between the first generator electrode and the second generator electrode to form an electric field between the first generator electrode and the second generator electrode, wherein the reference electrode is arranged between the first generator electrode and the second generator electrode whereby, due to the electric field upon the electric current becoming established, a defined reference potential becomes established on the reference electrode arranged between the first generator electrode and the second generator electrode.

12. An electrochemical gas sensor system in accordance with claim 11, wherein at least one of a halide compound or a halide is contained in the electrolyte liquid.

13. An electrochemical gas sensor system in accordance with claim 12, wherein:
- the halide compound contained in the electrolyte liquid or the halide contained in the electrolyte liquid is reacted by means of the electric circuit to form a halogen; and
- the defined reference potential established on the reference electrode is in a range of 935 mV+25 mV.

14. An electrochemical gas sensor system in accordance with claim 12, wherein:
- the halide compound contained in the electrolyte liquid or the halide contained in the electrolyte liquid is bromide, and reacts to form bromine by means of the electric circuit; and
- the defined reference potential established on the reference electrode is in a range of 935 mV±25 mV.

15. An electrochemical gas sensor system in accordance with claim 11, wherein the voltage generator comprises at least one of a settable voltage generator, a settable voltage source and a settable power source.

16. An electrochemical gas sensor system in accordance with claim 11, wherein the voltage generator comprises a battery.

17. An electrochemical gas sensor system in accordance with claim 11, further comprising:
- a nonwoven permeable to the electrolyte liquid arranged at the first generator electrode and
- a nonwoven permeable to the electrolyte liquid is arranged at the second generator electrode.

18. An electrochemical gas sensor system in accordance with claim 17, wherein the nonwoven permeable to the electrolyte liquid arranged each at the first generator electrode and at the second generator electrode set an installed position with predetermined distance of the first generator electrodes from the reference electrode, predetermined distance of the second generator electrodes from the reference electrode and a predetermined distance between the first generator electrode and the second generator electrode.

19. An electrochemical gas sensor system in accordance with claim 18, wherein the first generator electrode and the second generator electrode and the reference electrode and the nonwovens permeable to the electrolyte liquid are enclosed by an inner housing that is not permeable to the electrolyte liquid.

20. An electrochemical gas sensor system in accordance with claim 19, wherein at least one of the nonwovens, permeable to the electrolyte liquid, transports the electrolyte liquid from the sensor housing to an area between the first and second generator electrodes into the inner housing impermeable to the electrolyte liquid towards the first generator electrode and the second generator electrode.

* * * * *